US012427125B2

(12) United States Patent
Lee

(10) Patent No.: US 12,427,125 B2
(45) Date of Patent: Sep. 30, 2025

(54) METHOD FOR TREATING SARS AND TREATING OR PREVENTING ARDS

(71) Applicant: AARDVARK THERAPEUTICS, INC., San Diego, CA (US)

(72) Inventor: Tien-Li Lee, San Diego, CA (US)

(73) Assignee: Aardvark Therapeutics, Inc., San Diego, CA (US)

( * ) Notice: Subject to any disclaimer, the term of this patent is extended or adjusted under 35 U.S.C. 154(b) by 471 days.

(21) Appl. No.: 17/915,952

(22) PCT Filed: Mar. 20, 2021

(86) PCT No.: PCT/US2021/023361
§ 371 (c)(1),
(2) Date: Sep. 29, 2022

(87) PCT Pub. No.: WO2021/194910
PCT Pub. Date: Sep. 30, 2021

(65) Prior Publication Data
US 2023/0149328 A1 May 18, 2023

Related U.S. Application Data

(60) Provisional application No. 62/993,020, filed on Mar. 22, 2020.

(51) Int. Cl.
| | | |
|---|---|---|
| *A61K 31/167* | (2006.01) | |
| *A61K 9/00* | (2006.01) | |
| *A61K 31/192* | (2006.01) | |
| *A61P 11/00* | (2006.01) | |
| *A61P 31/14* | (2006.01) | |

(52) U.S. Cl.
CPC .......... *A61K 31/167* (2013.01); *A61K 9/0053* (2013.01); *A61K 31/192* (2013.01); *A61P 11/00* (2018.01); *A61P 31/14* (2018.01)

(58) Field of Classification Search
CPC ......... A61K 9/0053; A61P 11/00; A61P 31/14
See application file for complete search history.

(56) References Cited

U.S. PATENT DOCUMENTS

| | | |
|---|---|---|
| 2004/0208833 A1 | 10/2004 | Hovey et al. |
| 2012/0121653 A1 | 5/2012 | Jenkins et al. |
| 2022/0193013 A1* | 6/2022 | Lee .......................... A61P 3/04 |

FOREIGN PATENT DOCUMENTS

WO    2008/021394 A2    2/2008

OTHER PUBLICATIONS

Centers for Disease Control and Prevention, "Severe Acute Respiratory Syndrome (SARS) Treatment," originally at www.cdc.gov/ncidod/sars/treatment, currently available at https://web.archive.org/web/20030404183759/http://www.cdc.gov:80/ncidod/sars/treatment.htm, 1 page (Mar. 25, 2003).
Clark et al., "Preliminary Clinical Description of Severe Acute Respiratory Syndrome," Morbidity and Mortality Weekly Report, 52(12): 255-256 (2003).
Cyranoski, "Critics slam treatment for SARS as ineffective and perhaps dangerous," Nature, 423: 4 (2003).
Poutanen et al., "Identification of Severe Acute Respiratory Syndrome in Canada," N. Engl. J. Med., 348(20):1995-2005 (2003).
Rane et al., "Development of solitary chemosensory cells in the distal lung after severe influenza injury," Am. J. Physiol. Lung Cell Mol. Physiol., 316: L1141-L1149 (2019).
Rota et al., "Characterization of a Novel Coronavirus Associated with Severe Acute Respiratory Syndrome," Science, 300: 1394-1399 (2003).
Song et al., "From SARS to MERS, Thrusting Coronaviruses into the Spotlight," Viruses, 11(59): 28 pages (2019).
Wikipedia, "Severe acute respiratory syndrome," retrieved from https://en.wikipedia.org/w/index.php?title=Severe_acute_respiratory_syndrome&oldid=94349864002, edited Mar. 2, 2020 (14 pages).
L. Young, Authorized Officer, International Search Report and Written Opinion mailed Jun. 21, 2021, for International Application No. PCT/US2021/023361, filed Mar. 20, 2021 (7 pages).

* cited by examiner

*Primary Examiner* — Andrew S Rosenthal
(74) *Attorney, Agent, or Firm* — McNeill PLLC

(57) ABSTRACT

There is disclosed compositions and methods for treating and preventing Acute Respiratory Distress Syndrome (ARDS) including ARDS caused by viral respiratory disease of zoonotic origin such as coronaviruses. The present disclosure is based on a surprising discovery of significant efficacy in an acute lung injury model using intrapulmonary lipopolysaccharide (LPS) challenge in female CD-I mice. Based on these data, the test compound, denatonium acetate monohydrate (DA) (1) treats or prevents ARDS and, (2) treats severe acute respiratory syndrome (SARS) caused by a coronavirus. Therefore, the data achieved in these studies does have a story to tell and the story is that a DA pharmaceutical composition, administered orally, provided a method to treat or prevent ARDS and treat SARS. Preferably, the pharmaceutical composition for daily administration comprises DA delivering a daily total dose of from about 20 mg to about 2000 mg to a human adult.

14 Claims, 2 Drawing Sheets

METHOD FOR TREATING SARS AND TREATING OR PREVENTING ARDS

This application is a national phase entry pursuant to 35 U.S.C. § 371 of International Application No. PCT/US2021/023361, filed Mar. 20, 2021, which claims priority to U.S. Provisional Application No. 63/993,020, filed on Mar. 22, 2020, the disclosures of each of which are hereby incorporated by reference in their entireties.

TECHNICAL FIELD

The present disclosure provides compositions and methods for treating and preventing Acute Respiratory Distress Syndrome (ARDS) including ARDS caused by viral respiratory disease of zoonotic origin such as coronaviruses. The present disclosure is based on a surprising discovery of significant efficacy in an acute lung injury model using intrapulmonary lipopolysaccharide (LPS) challenge in female CD-1 mice. Based on these data, the test compound, denatonium acetate monohydrate (DA) (1) treats or prevents ARDS and, (2) treats severe acute respiratory syndrome (SARS) caused by a coronavirus. Therefore, the data achieved in these studies does have a story to tell and the story is that a DA pharmaceutical composition, administered orally, provided a method to treat or prevent ARDS and treat SARS. Preferably, the pharmaceutical composition for daily administration comprises DA delivering a daily total dose of from about 20 mg to about 2000 mg to a human adult.

BACKGROUND

ARDS is a critical illness characterized by acute lung injury leading to non-cardiogenic pulmonary edema, which in turn results in diffuse alveolar damage, respiratory failure, and hypoxemia. Despite significant advances in critical care management, mortality from ARDS remains at 40-70%. Current treatment is predominantly support of the respiratory system with, for example, mechanical ventilation.

In general, the development of ARDS can be separated into two phases: an initiator stage followed by an effector stage. The initiator phase of ARDS involves the release of inflammatory mediators (i.e. cytokines; complement and coagulation factors; and arachidonic acid metabolites) which promote systemic inflammation resulting in pulmonary neutrophil sequestration. The second stage, the effector phase, involves the activation of neutrophils with subsequent release of toxic oxygen radicals and proteolytic enzymes, specifically neutrophil elastase (NE). NE has the capacity to injure pulmonary endothelial cells and degrade products of the extracellular matrix, such as elastin, collagen, and fibronectin which comprise the lung basement membrane.

Many diverse forms of ARDS exist with disparate etiologies and courses, although the end-state pathologies of these diverse forms are the same. Examples of clinical events that may precipitate different forms of ARDS include trauma, hemorrhage, diffuse pneumonia, virally induced pneumonia (including, but not limited to COVID-19 and SARS), inhalation of toxic gases, and sepsis. In the case of the 2020 COVID-19 pandemic, it is a viral pneumonia that drives the ARDS observed in many patients requiring critical care. Irrespective of initial cause, ARDS has the following in common: intrapulmonary fluid accumulation and exudates leading to diffuse alveolar damage and impaired gas exchange in the alveoli. What is common (irrespective of the initial cause of the ARDS) downstream is a worsening due to inflammation, fluid release, cell migration and proliferation as well as increases of proinflammatory cytokines.

SARS is a respiratory illness that has been reported in around 2002-2.003. But more recently, COVID-19 (also known as SARS-Cov-2 or SARS-2) has become a pandemic in 2020. COVID-19 is an infectious disease that is highly contagious with significant, morbidity and mortality. Originating in Asia, the virus has infected approximately hundreds of thousands of individuals when this is being written on 20 Mar. 2020). A high percentage of resulting fatalities have ARDS as the ultimate cause of death. SARS is a significant threat to the health and welfare of the human population worldwide, and efforts are currently underway to develop treatments for the disease.

Viral respiratory infection is generally characterized by an incubation period typically 2-7 days in length, with infected individuals typically exhibiting high fevers, sometimes with accompanying chills, headache, malaise and myalgia. Viral infection of the lungs accounts for approximately 10-15% of ICU admissions in the US per year without a pandemic and is responsible for a significant percentage of deaths from influenza each year without a coronavirus pandemic. The 2020 pandemic from COVID-19 illustrates this course of disease progression. The illness progresses with the onset of a dry, non-productive cough or dyspnea, accompanied by or advancing into hypoxemia. A significant number of cases require intubation and mechanical ventilation. Furthermore, a the peak of respiratory illness, approximately 50% of infected individuals develop leukopenia and thrombocytopenia (*MMWR Moth Mortal Wkly Rep.* 2003 Mar. 28; 52(12):255-6).

The patterns by which viral load spreads (such as a coronavirus or influenza virus) suggest droplet or contact transmission of a viral pathogen (*N. Engl. J. Med.* 2003 May 15; 348(20):1995-2005). SARS-1 and -2 have been associated etiologically with a virus, SARS-associated coronavirus (SARS-CoV) is a member of the coronavirus family of enveloped viruses which replicate in the cytoplasm of infected animal host cells. Corona viruses are generally characterized as single-stranded RNA viruses having genomes of approximately 30,000 nucleotides (*Science.* 2003 May 30; 300(5624):1394-9). Coronaviruses fall into three known groups; the first two groups cause mammalian coronavirus infections, and the third group causes avian coronavirus infections (J. S. M. Peiris, in Medical Microbiology (Eighteenth Edition), 2012, 587-593). Corona viruses are believed to be die causative agents of several severe diseases in many animals, for example, infectious bronchitis virus, feline infectious peritonitis virus and transmissible gastroenteritis virus, are significant veterinary pathogens (*Viruses.* 2019 January; 11(1): 59).

As of Mar. 25, 2003, the U.S. Centers for Disease Control and Prevention stated that "[n]o specific treatment recommendations can be made at this time." (*CDC SARS Treatment*, www.edc.gov/ncidod/sars/treatment). One therapy currently administered in Hong Kong, a combination of steroids and the antiviral agent ribavirin, has been criticized as ineffective and even dangerous to recipients (*Nature.* 2003 May 1; 423(6935):4). Other attempted therapies have included administration of antibiotics or oseltamivir (*N. Engl. J Med.* 2003 May 15; 348(20):1995-2005). In the absence of an effective treatment, healthcare workers are limited to using supportive measures, such as intravenous (IV) fluids, oxygen and, when necessary, mechanical ventilation and intubation, to treat patients having SARS.

Accordingly, a need exists for an effective treatment for patients diagnosed with SARS, patients infected with an infectious agent associated with SARS, such as patients infected with a SARS-CoV, or patients at imminent risk of contracting SARS, such as individuals that were exposed, or probably will be exposed in the near future, to an infectious agent associated with SARS. The prior art treatments for ARDS are inadequate. Accordingly, there is an urgent need for an effective treatment of ARDS.

SUMMARY

The present disclosure provides compositions and methods for treating and preventing Acute Respiratory Distress Syndrome (ARDS) including ARDS caused by viral respiratory disease of zoonotic origin such as coronaviruses. The present disclosure is based on a surprising discovery of significant efficacy in an acute lung injury model using intrapulmonary lipopolysaccharide (LPS) challenge in female CD-1 mice. Based on these data, the test compound, denatonium acetate monohydrate (DA) (1) treats or prevents ARDS and, (2) treats severe acute respiratory syndrome (SARS) caused by a coronavirus. Therefore, the data achieved in these studies does have a story to tell and the story is that a denatonium salt pharmaceutical composition, administered orally, provided a method to treat or prevent ARDS and treat SARS. Preferably, the pharmaceutical composition for daily administration comprises DA delivering a daily total dose of from about 20 mg to about 2000 mg to a human adult.

The present disclosure provides a pharmaceutical composition for treatment of SARS comprising a denatonium salt, wherein the denatonium salt is selected from the group consisting of denatonium acetate (DA) denatonium citrate, denatonium maleate, denatonium saccharide, and denatonium tartrate. Preferably, the pharmaceutical composition further comprises from about 0.5 g to about 5 g acetic acid. More preferably, the dosage per day of the acetic acid for an adult is from about 1.5 g to about 3 g. Preferably the daily dosage of the denatonium salt for an adult is from about 10 mg to about 600 mg or from about 5 mg/kg to about 50 mg/kg body weight per day. Most preferably, the daily dosage of DA for an adult is from about 10 mg to about 400 mg, or to achieve a concentration in the GI tract of from about 10 parts per billion to about 10 ppm. The daily dose of the denatonium salt is administered once per day, twice per day or three times per day.

The present disclosure further provides method for treating or preventing ARDS comprising administering an effective amount of a pharmaceutical formulation comprising a denatonium salt, wherein the denatonium salt is selected from the group consisting of denatonium acetate (DA) denatonium citrate, denatonium maleate, denatonium saccharide, and denatonium tartrate. Preferably, the pharmaceutical composition further comprises from about 0.5 g to about 5 g acetic acid. More preferably, the dosage per day of the acetic acid for an adult is from about 1.5 g to about 3 g. Preferably the daily dosage of the denatonium salt for an adult is from about 10 mg to about 600 mg or from about 5 mg/kg to about 50 mg/kg body weight per day. Most preferably, the daily dosage of DA for an adult is from about 10 mg to about 400 mg, or to achieve a concentration in the GI tract of from about 10 parts per billion to about 10 ppm. The daily dose of the denatonium salt is administered once per day, twice per day or three times per day.

Figure 1:
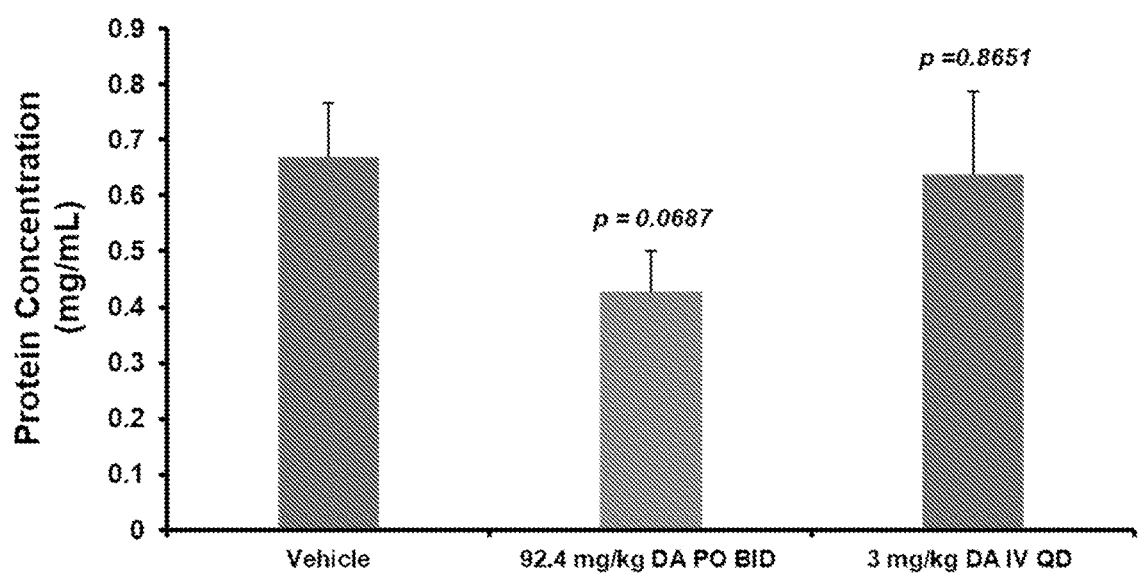
FIG. 1 shows the protein concentration measurements of two DA doses given orally (PO) and iv. Only oral administration was effective. These data show a less protein-rich fluid after oral dosing.

DETAILED DESCRIPTION present disclosure provides compositions and methods for treating patients, including humans, who are infected by a pathogenic agent associated with SARS, including suspected, probable and confirmed cases of SARS.

As used herein, the expression "SARS patient" refers to a mammalian patient, such as a human, who is confirmed to have SARS or COVID-19 or who may be classified as having a probable or suspected case of SARS based on epidemiological factors. SARS patients include those who are diagnosed with SARS, those who test positive for infection by an infectious agent (pathogen) associated with SARS (e.g., SARS-CoV-1 or -2), those who are suspected of having SARS based on epidemiological factors, or those who are at an imminent risk of contracting SARS (e.g., one who has been exposed or will likely be exposed to SARS in the near future). The term "SARS patient" is used interchangeably herein with the expressions "patient having SARS," "patient infected with SARS," "patient with SARS", "patients suffering from SARS" and other such expressions.

The phrase "therapeutically effective amount," as used herein, refers to the amount to be administered to a mammalian host (preferably human) in each single dose (as part of a series of doses) to at least cause the individual treated to generate a response that reduces the clinical impact of the infection. This may range from a minimal decrease in pathogenic burden to prevention of the infection. Ideally, the treated individual will not exhibit the more serious clinical manifestations of the infection. The dosage amount can vary depending upon specific conditions of the individual. The specific amount to administer can be determined in routine trials or otherwise by means known to those sf filled in the art, based upon the guidance provided herein.

The phrase "administering a therapeutically effective amount" of a therapeutic agent means that the patient is treated with the agent in an amount and for a time sufficient to induce a sustained improvement over baseline in at least one indicator that reflects the severity of the disorder. An improvement is considered "sustained" if the patient exhibits the improvement on at least two occasions separated by one or more weeks. The degree of improvement is determined based on signs or symptoms, and determinations may also employ questionnaires that are administered to the patient, such as quality-of-life questionnaires.

Therapeutic Administration

The denatonium salt is administered with symptomatic patients that are admitted to a regular floor and track how many patients eventually testing positive fall into ARDS or ICU admission. Preferably dosing should begin either at start of symptoms or, at a later stage of development, in addition when expected exposure. It should be noted that starting at mild symptoms is that that is mostly too late already for antivirals. But too soon for other aggressive treatments. Further, the effect is beneficial for many respiratory viruses, therefore it is not necessary to have to wait for a positive coronavirus test before initiating treatment.

Denatonium Salt Compound

TABLE 1

| Denatonium salts | |
|---|---|
| name | chemical structure |
| Denatonium acetate | (structure shown) |

Synthesis of Denatonium Acetate

Step 1: Synthesis of Denatonium Hydroxide from Lidocaine

To a reflux apparatus add 25 g of lidocaine, 60 mL of water and 17.5 g of benzyl chloride with stirring and heating in 70-90° C. The solution needs to be heated and stirred in the before given value for 24 h, the solution needs to be cooled down to 30° C. The unreacted reagents are removed with 3×10 mL of toluene. With stirring dissolve 65 g of sodium hydroxide into 65 mL of cold water and add it to the aqueous solution with stirring over the course of 3 h. Filter the mixture, wash with some water and dry in open air. Recrystallize in hot chloroform or hot ethanol.

Step 2: Preparation of Denatonium Acetate from Denatonium Hydroxide.

To a reflux apparatus 10 g of denatonium hydroxide (MW: 342.475 g/mol, 0.029 mol), 20 mL of acetone, and 2 g of acetic acid glacial (0.033 mol) dissolved in 15 mL of acetone is added, the mixture is stirred and heated to 35° C. for 3 h. Then evaporated to dryness and recrystallized in hot acetone.

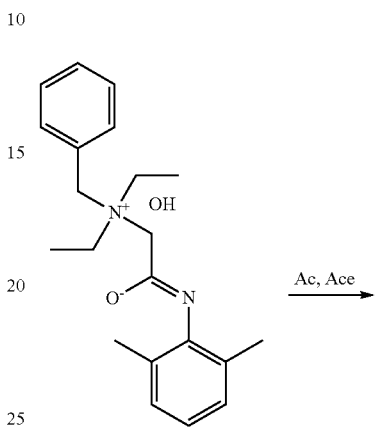

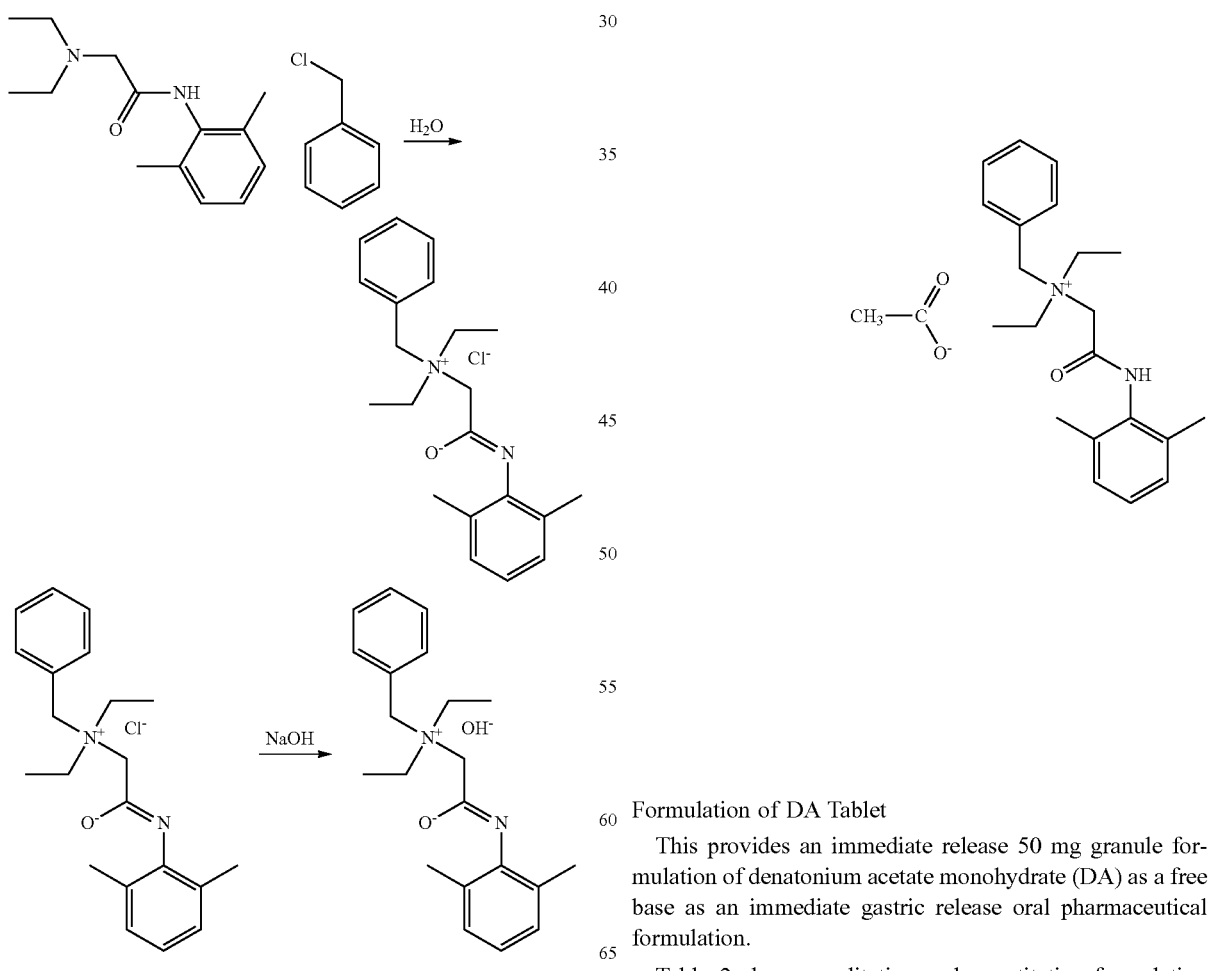

Formulation of DA Tablet

This provides an immediate release 50 mg granule formulation of denatonium acetate monohydrate (DA) as a free base as an immediate gastric release oral pharmaceutical formulation.

Table 2 shows qualitative and quantitative formulation composition of DA.

| Ingredient | Quality Standard | Function | Quantity (%) w/w | DA capsule-50 mg (mg/cap) | Max Potency for Unit Dose (mg) — Limits based on IID | Reference |
|---|---|---|---|---|---|---|
| Denatonium acetate monohydrate | In-house | API | 23.55 | 59.03 (20 mg Denatonium base) | N/A | N/A |
| Povidone (KOLLIDON 30) | USP | Binder | 2.36 | 5.90 | 61.5 | Oral - Capsule |
| Sugar Spheres (VIVAPHARM ® Sugar Spheres 35-45) | NF | Substrate | 68.85 | 172.57 | 314.13 | Oral - Capsule |
| Hypromellose (Methocel E5 Premium LV Hydroxypropyl Methylcellulose) | USP | Binder | 3.64 | 9.14 | 150 | Oral - Capsule |
| Talc (MicroTalc MP 1538 USP Talc) | USP | Anti-tacking agent | 1.09 | 2.74 | 14 | Oral - Capsule, coated pellets |
| Talc (extra granular) (MicroTalc MP 1538 USP Talc) | USP | Flow aid | 0.50 | 1.25 | 284.38 | Oral - Capsule |
| Total weight of beads | | | | 250.62 | N/A | N/A |
| Hard Gelatin Capsule Shells; Cap: White Opaque; Body: White Opaque; Size: 1 | USP | Capsule shell | N/A | 73.3 | 107 | Oral - Capsule |
| Total weight of Filled Capsule | | | | 323.9 | N/A | N/A |

IID, the Inactive Ingredient Database;
API, active pharmaceutical ingredient;
USP, the US Pharmacopeia;
NF, the National Formulary
* Solvents such as Ethyl Alcohol USP 190 Proof (190 Proof Pure Ethyl Alcohol) and purified water (USP) were used for the preparation of drug solution and seal coating dispersion, but are removed during the manufacturing process.

The detailed manufacturing steps are described below.

1. Drug Layering Process—Drug Layered Pellets

Drug layering process was performed in a Fluid bed granulator equipped with the rotor insert (rotor granulator). Drug solution was prepared by solubilizing Povidone K30 (Kollidon 30) and Denatonium Acetate in ethyl alcohol. The drug solution was sprayed tangentially on to the bed of sugar spheres (35/45 mesh) moving in a circular motion in the rotor granulator. The final drug loaded pellets were then dried for ten (10) minutes in the rotor granulator, discharged and screened through a #20 mesh.

2. Seal Coating Process—Seal Coated Pellets

Seal coating dispersion was prepared by separately dissolving Hypromellose E5 in a mixture (1:1) of ethyl alcohol and purified water until a clear solution was obtained. The remaining quantity of ethyl alcohol was then added to the above solution followed by talc. The dispersion was mixed for 20 minutes to allow for uniform dispersion of talc. The seal coating dispersion was sprayed tangentially on to the drug loaded pellets to achieve 5% weight gain. The seal coated pellets were then dried for five (5) minutes in the rotor granulator, discharged and dried further in a tray dryer/oven at 55° C. for 2 hours. The seal coated pellets were then screened through a #20 mesh.

3. Final Blending—Denatonium Immediate Release (IR) Pellets

The seal coated pellets were blended with talc screened through mesh #60 using a V-Blender for ten (10) minutes and discharged. The blended seal coated beads, Denatonium IR Pellets, were used for encapsulation.

4. Encapsulation—Denatonium Capsules, 50 mg

The Denatonium IR pellets, 50 mg, were filled into size 1, white opaque hard gelatin capsules using an auto capsule filling machine. Capsules were then passed through an in-line capsule polisher and metal detector. In-process controls for capsule weight and appearance was performed during the encapsulation process. Acceptable quality limit (AQL) sampling and testing was performed by Quality Assurance (QA) on a composite sample during the encapsulation process. Finished product composite sample was collected and analyzed as per specification for release testing.

5. Packaging—Capsules, 50 mg-30 Counts

The 50 mg capsules were packaged in 30 counts into 50/60 cc White HDPE round S-line bottles with 33 mm White CRC Caps. The bottles were torqued and sealed using an induction sealer.

Example 1

This example describes two in vivo studies of oral DA in a mouse acute lung injury model following LPS administration in female CD-1 mice. The protocols obtained 30 or 18 female CD-1 mice (Charles River Lab) and monitored daily for body condition and health status during the 3-5 days acclimation period. For the first study, starting three days before the induction of lung injury, groups of 10 CD-1 mice each were treated prophylactically with vehicle or 92.4 mg/kg DA (administered by twice-daily (BID) oral gavage (PO)) or with 3 mg/kg DA (administered by once-daily (QD) intravenous (iv) injection). For the second study, the same procedure was used, and groups of six CD-1 mice each were treated prophylactically with vehicle or 92.4 mg/kg DA (administered by BID, PO) or with 3 mg/kg DA (administered by QD intraperitoneal (ip) injection).

At time 0, the mice were weighed. LPS was prepared 1 mg LPS in 1 ml phosphate buffered saline (PBS) to get a final concentration of 1 mg/mL. Dosed 50 µl intratracheally to the mice at time 0. For the N=30 or 18 mice in an incubator, temperature was set to achieve a core temperature of 39° C. as measured by a calibrated thermometer inserted through the top lid of the incubator with the bulb at the level of the mouse cages in the incubator (set temperature knob at 36.7° C.). In addition, a rectal probe to confirmed core temperature in the mice (check right before sacrifice at 24 h post LPS). All mice were given access to food and water at all time. Treatment was initiated three days prior to LPS dosing.

For anesthesia and LPS Dosing, mice were placed in a bell jar, with isoflurane-soaked gauze separated from the mouse by a screen and keep within a scrubber (so the operator isn't anesthetized). Monitored respiratory rate of each mouse and when reduced by half (usually within 5 seconds of going down), then take the mouse out. Each mouse was suspended from incisors across a string tied between two screws on a Plexiglas board and kept at about 70 degrees. Using blunt forceps, grabbed the tongue and hold extended, then instill 50 µL of the LPS solution into the oropharynx using a PennCentury needle/areosolizer. The liquid disappeared from the oropharynx at the same time. Mouse kept in this position for 5-10 seconds to allow distribution of the LPS, then returned to their cage.

Bronchoalveolar lavage fluid (BALF) was collected using rounded tip scissors make a vertical incision though skin but not peritoneum from the lower abdomen up to the jaw. Using two forceps grabbed the edge of the skin and pull apart to get wide exposure to underlying peritoneum and thoracic connective tissue/muscle. Using forceps, picked up peritoneum near the mid abdomen and with rounded tip scissors made a small incision in the peritoneum (avoid cutting gut). Then, while holding the upper edge of the peritoneum, used the rounded tip scissors to extend the incision diagonally to the left upper and right upper quadrants. Moved the liver and intestines out of the way so you can see the underside of the diaphragms. Using the rounded tip scissors, nibbled up toward the diaphragm until you can see the lungs on the other side pull away. Repeated on the other side, being careful to not nick the lungs or else you will not be able to recover lavage. Using the rounded tip scissors, cut through the diaphragm where it inserts on the anterior chest wall. Using the rounded tip scissors and taking care to avoid nicking the lung by moving it away with blunt forceps, cut through the chest wall laterally on both sides until you reach the top of the thorax, then cut across the midline at the top to remove the anterior chest wall. Using forceps pull upward on the heart and cut through at its base to remove. Using the rounded tip scissors, remove the fat pads overlying the trachea taking care not to nick the trachea. Using the rounded tip scissors inserted next to the trachea from the top of the thoracic cavity and kept next to and parallel to the trachea, make a single cut, which allowed removal of the rest of the soft tissue from the trachea but pulling over to the other side and carefully trimming to avoid nicking the trachea. Using sharp forceps carefully placed posterior to the trachea pull suture behind the trachea about 4-5 mm below the cricoid and made a very loose surgical knot (two loops around). Using ophthalmic scissors, very carefully made a cut through the anterior half of the trachea just below the cricoid. Inserted a short blunt needle into tracheal so the tip extended about 5-6 mm below the cricoid and tied a suture tightly with a second knot. Used a 1 mL Luer lock syringe loaded with 1 mL PBS to instill and then withdraw the lavage fluid. Had to maintain a little upward traction to avoid the tip of the needle hitting the carina and obstructing the lumen. Avoided twisting the trachea as this will obstruct the lumen. The first 1 ml PBS was infused and withdrawn and then reinfused without disconnecting the syringe. A second 1 mL aliquot of PBS in a fresh syringe was infused and withdrawn only once. The contents of the two syringes were pooled for analysis of protein and cells. The usual recovery was about 1.5 ml. The BALF was centrifuged in a microcentrifuge at 5000 rpm for 3 minutes, and the supernatant collected and analyzed for protein using the Bradford method (Biorad) and a bovine serum albumin standard curve. Cytokine concentrations in the BALF were measured using a Millipore mouse 32plex kit. For the second study, in addition to protein level and cytokine concentration assessments, the BALF specimens were assessed for neutrophil counts by fluorescence-activated cell sorting (FACS) with gating for $Ly6G^+/CD11b^+$ cells.

For the first study, three days of repeat PO dosing with 92.4 mg/kg DA (BID) or IV dosing with 3 mg/kg DA (QD) was well-tolerated in CD-1 mice. Although three mice [two vehicle-dosed, one DA (92.4 mg/kg)-dosed] were found dead on Day 1, the timing of these mortalities (within 24 h after LPS instillation) suggested that the deaths reflected the instillation process or associated inflammation (rather than test article). This inference is consistent with the observation that deaths were seen both with vehicle and test article dosing. No other adverse clinical observations were noted during 3 days of test article administration.

Table 3 and FIG. 1 show the protein concentration measurements of two DA doses given orally (PO) and iv. Only oral administration was effective. These data show a less protein-rich fluid after oral dosing.

TABLE 3

BALF Protein Concentrations of the First Mouse Acute Lung Injury Study

| Group | Animal No. | OD Rep. 1 | OD Rep. 2 | OD Mean | Blank-adjusted | Protein Concentration (mg/mL) Per Mouse | Mean | SE | p value [a] |
|---|---|---|---|---|---|---|---|---|---|
| Vehicle | 1.1 | 1.174 | 1.158 | 1.166 | 1.081 | 1.12 | 0.669 | 0.097 | NA |
| (PO, BID) | 1.2 | 0.856 | 0.833 | 0.844 | 0.760 | 0.79 | | | |
| | 1.3 | fd | | | | | | | |
| | 1.4 | 0.959 | 0.933 | 0.946 | 0.861 | 0.90 | | | |
| | 1.5 | 0.382 | 0.371 | 0.376 | 0.291 | 0.31 | | | |
| | 1.6 | 0.570 | 0.596 | 0.583 | 0.498 | 0.52 | | | |
| | 1.7 | fd | | | | | | | |
| | 1.8 | 0.653 | 0.654 | 0.654 | 0.569 | 0.59 | | | |
| | 1.9 | 0.822 | 0.798 | 0.810 | 0.725 | 0.75 | | | |
| | 1.10 | 0.450 | 0.424 | 0.437 | 0.352 | 0.37 | | | |
| DA | 2.1 | 0.484 | 0.464 | 0.474 | 0.389 | 0.41 | 0.428 | 0.073 | 0.0687 |
| 92.4 mg/kg | 2.2 | 0.585 | 0.581 | 0.583 | 0.498 | 0.52 | | | |
| (PO, BID) | 2.3 | 0.185 | 0.169 | 0.177 | 0.092 | 0.10 | | | |
| | 2.4 | 0.654 | 0.710 | 0.682 | 0.597 | 0.62 | | | |
| | 2.5 | fd | | | | | | | |
| | 2.6 | 0.428 | 0.433 | 0.430 | 0.345 | 0.36 | | | |
| | 2.7 | 0.355 | 0.363 | 0.359 | 0.274 | 0.29 | | | |
| | 2.8 | 0.708 | 0.660 | 0.684 | 0.599 | 0.62 | | | |
| | 2.9 | 0.829 | 0.785 | 0.807 | 0.722 | 0.75 | | | |
| | 2.10 | 0.265 | 0.235 | 0.250 | 0.165 | 0.18 | | | |
| DA | 3.1 | 0.568 | 0.522 | 0.545 | 0.460 | 0.48 | 0.638 | 0.150 | 0.8651 |
| 3 mg/kg | 3.2 [b] | 1.916 | 1.926 | 1.921 | 1.836 | 1.90 | | | |
| (IV, QD) | 3.3 | 0.620 | 0.639 | 0.630 | 0.545 | 0.57 | | | |
| | 3.4 | 0.324 | 0.321 | 0.322 | 0.237 | 0.25 | | | |
| | 3.5 | 0.898 | 0.909 | 0.904 | 0.819 | 0.85 | | | |
| | 3.6 | 0.549 | 0.562 | 0.556 | 0.471 | 0.49 | | | |
| | 3.7 | 0.553 | 0.556 | 0.554 | 0.469 | 0.49 | | | |
| | 3.8 | 0.388 | 0.401 | 0.395 | 0.310 | 0.33 | | | |
| | 3.9 | 0.667 | 0.686 | 0.676 | 0.591 | 0.62 | | | |
| | 3.10 | 0.476 | 0.460 | 0.468 | 0.383 | 0.40 | | | |

BID, twice daily.
DA, denatonium acetate.
fd, found dead (gray-shaded cells).
IV, intravenous.
NA, not applicable.
OD, optical density (562 nm).
PO, by mouth (oral gavage).
QS, once daily.
Rep., replicate.
[a] p value by two-tailed non-paired t-test vs. Group 1 (vehicle). A difference was considered statistically significant with $p < 0.05$.
[b] Values for Mouse 3.2 are outliers. If data for No. 3.2 are excluded, Group 3 yields a mean ± SE of 0.498 ± 0.058 mg/mL and a p value (vs. Group 1) of 0.1570.

For the second study, three days of repeat PO dosing with 92.4 mg/kg DA (BID) or ip dosing with 3 mg/kg DA (QD) was well-tolerated in female CD-1 mice. Although two mice [one vehicle-dosed, one DA (92.4 mg/kg)-dosed] were found dead on Day 1, the timing of these mortalities (within 24 h after LPS instillation) suggested that the deaths reflected the instillation process, hyperthermia, or associated inflammation (rather than test article). This inference is consistent with the observation that deaths were seen both with vehicle and test article dosing. No other adverse clinical observations were noted during 3 days of test article administration.

Oral and IP dosing with the indicated levels of DA was associated with nominal (but non-significant) changes in BALF protein concentrations (Table 4).

TABLE 4

BALF Protein Concentrations of the Second Mouse Acute Lung Injury Study

| Treatment Group | Animal No. | $OD_{562\,nm}$ Rep 1 | Rep 2 | Mean | Blank-adjusted Value | Protein Conc. (mg/mL) Per Mouse | Mean | SE | vs. Group 1 p value |
|---|---|---|---|---|---|---|---|---|---|
| Vehicle | 1.2 | 1.02 | 1.03 | 1.025 | 0.933 | 0.87 | 0.913 | 0.119 | NA |
| | 1.3 | 1.20 | 1.20 | 1.200 | 1.107 | 1.05 | | | |
| | 1.4 | 0.80 | 0.80 | 0.801 | 0.708 | 0.65 | | | |
| | 1.5 | 1.48 | 1.43 | 1.456 | 1.363 | 1.30 | | | |
| | 1.6 | 0.85 | 0.85 | 0.847 | 0.755 | 0.70 | | | |

TABLE 4-continued

BALF Protein Concentrations of the Second Mouse Acute Lung Injury Study

| Treatment Group | Animal No. | OD$_{562\,nm}$ Rep 1 | Rep 2 | Mean | Blank-adjusted Value | Protein Conc. (mg/mL) Per Mouse | Mean | SE | vs. Group 1 p value |
|---|---|---|---|---|---|---|---|---|---|
| DA      | 2.1 | 1.30 | 1.30 | 1.297 | 1.204 | 1.14 | 0.986 | 0.065 | 0.611 |
| 92.4 mg/kg | 2.2 | 0.90 | 0.90 | 0.901 | 0.809 | 0.75 | | | |
| (PO, BID) | 2.3 | 1.10 | 1.13 | 1.116 | 1.023 | 0.96 | | | |
|         | 2.4 | 1.20 | 1.19 | 1.197 | 1.104 | 1.04 | | | |
|         | 2.5 | 1.19 | 1.19 | 1.186 | 1.094 | 1.03 | | | |
| DA      | 3.1 | 0.77 | 0.77 | 0.769 | 0.677 | 0.62 | 0.727 | 0.083 | 0.238 |
| 3 mg/kg | 3.2 | 0.93 | 0.93 | 0.930 | 0.838 | 0.78 | | | |
| (IP, QD) | 3.3 | 1.26 | 1.26 | 1.262 | 1.169 | 1.11 | | | |
|         | 3.4 | 0.85 | 0.86 | 0.857 | 0.764 | 0.71 | | | |
|         | 3.5 | 0.68 | 0.69 | 0.686 | 0.593 | 0.54 | | | |
|         | 3.6 | 0.77 | 0.76 | 0.761 | 0.669 | 0.61 | | | |

BID, twice daily.
DA, denatonium acetate.
IP, intraperitoneal.
NA, not applicable.
OD, optical density.
PO, by mouth (oral gavage).
QD, once daily.
Rep., replicate.
[a] p value by two-tailed non-paired t-test vs. Group 1 (vehicle). A difference was considered statistically significant with $p < 0.05$.

TABLE 5

BALF Neutrophil Counts (FACS with Gating for Ly6G$^+$/CD11b$^+$ Cells)

| Treatment Group | Animal No. | Neutrophils (cells/μL) | Dilution Factor | Total Vol. (μL) | Per Sample | Total Neutrophil Count per Lavage Mean | SE | vs. Group 1 p value [a] |
|---|---|---|---|---|---|---|---|---|
| Vehicle | 1.2 | 2585 | 0.6 | 500 | 775,500   | 688,320 | 82,896  | NA |
|         | 1.3 | 1524 | 0.6 | 500 | 457,200   |         |         |    |
|         | 1.4 | 3110 | 0.6 | 500 | 933,000   |         |         |    |
|         | 1.5 | 2379 | 0.6 | 500 | 713,700   |         |         |    |
|         | 1.6 | 1874 | 0.6 | 500 | 562,200   |         |         |    |
| DA      | 2.1 | 3604 | 0.6 | 500 | 1,081,200 | 535,080 | 143,990 | 0.3899 |
| 92.4 mg/kg | 2.2 | 1408 | 0.6 | 500 | 422,400   |         |         |    |
| (PO)    | 2.3 | 1500 | 0.6 | 500 | 450,000   |         |         |    |
|         | 2.4 | 1649 | 0.6 | 500 | 494,700   |         |         |    |
|         | 2.5 | 757  | 0.6 | 500 | 227,100   |         |         |    |
| DA      | 3.1 | 1152 | 0.6 | 500 | 345,600   | 610,900 | 91,832  | 0.5470 |
| 3 mg/kg | 3.2 | 2316 | 0.6 | 500 | 694,800   |         |         |    |
| (IP)    | 3.3 | 3081 | 0.6 | 500 | 924,300   |         |         |    |
|         | 3.4 | 1681 | 0.6 | 500 | 504,300   |         |         |    |
|         | 3.5 | 2598 | 0.6 | 500 | 779,400   |         |         |    |
|         | 3.6 | 1390 | 0.6 | 500 | 417,000   |         |         |    |

BID, twice daily.
DA, denatonium acetate.
IP, intraperitoneal.
NA, not applicable.
PO, by mouth (oral gavage).
QD, once daily.
[a] p value by two-tailed non-paired t-test vs. Group 1 (vehicle). A difference was considered statistically significant with $p < 0.05$.

Figure 2:
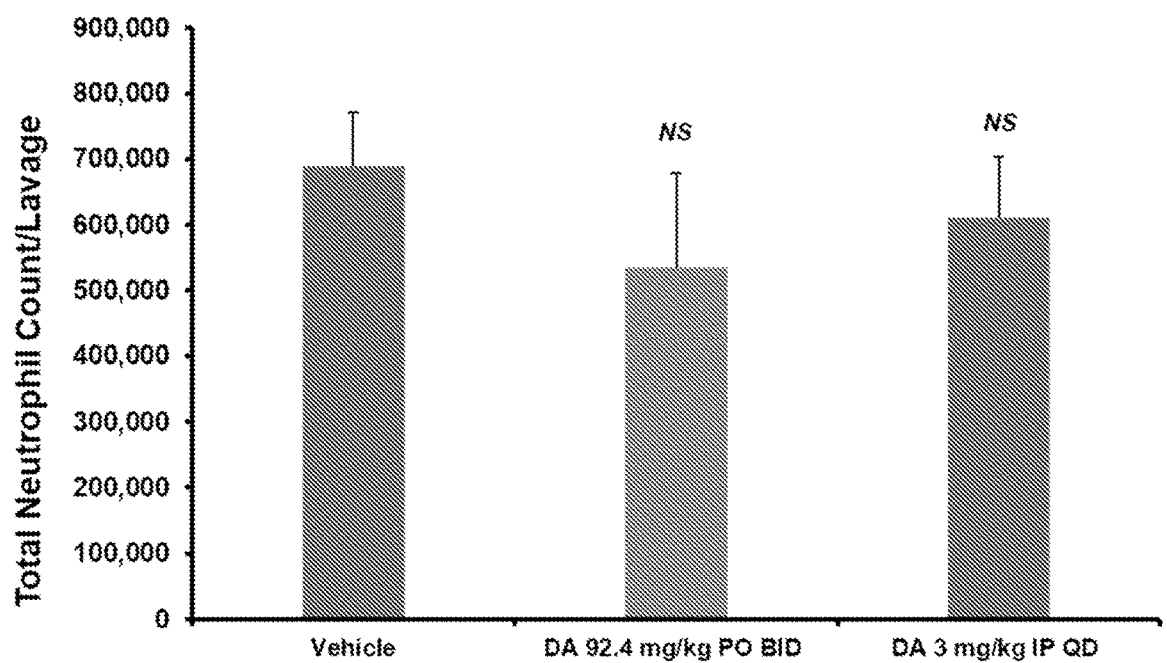
FIG. 2 shows the total neutrophil count of two DA doses given PO and ip. Only oral administration was effective. These data show a less neutrophil-rich fluid after oral dosing.

Table 5 and FIG. 2 show the total neutrophil count of two DA doses given PO and ip. Only oral administration was effective. These data show a less neutrophil-rich fluid after oral dosing.

Example 2

This example provides oral efficacy of DA in Treating BARS and preventing or treating ARDS in a randomized controlled study. As many as possible adult patients (i.e. eighteen years of age or older) laboratory-confirmed as being infected by SARS-CoV-19 (COVID-19) and hospitalized at risk for developing ARDS or having developed ARDS, are administered oral DA at doses of 30 mg/kg, 60 mg/kg or 100 mg/kg BID for up to ten days. Clinical assessment, vital signs, and laboratory parameters are measured before, during and periodically for 28 days after the dosing and as per standard of care. Specifically, lung function and inflammatory response will be monitored.

Clinical Monitoring

Study specific patients are monitored for 24 hours after each dose for hemodynamic change, fever or other adverse events. Clinical response studies are comprised of the following parameters:

Vital signs are recorded every two hours from each dose, and at intervals following each dose. A complete physical examination is performed at screening and conclusion of the treatment course, in addition, patients are monitored by standard laboratory tests including complete blood count, C3 and C4 components of complement, IgM, IgM and IgA, serum electrolytes, creatinine, urea, alkaline phosphatase, aspartate transaminase and total bilirubin, as well as serum or plasma levels of TNFα and IL-6 or other parameters delineating the inflammatory response such as CRP and others. Urine analysis and culture, as well as PCR is performed, whichever is most adequate to monitor viral titers, are also be performed at each assessment point to determine levels of SARS-CoV present.

Response Assessment

The patients are assessed for response to the treatment at weeks 1 and 2 of the trial. The assessments are made between 0700 and 13 hours by the same observer. The following clinical assessments include: temperature, subjective feelings of respiratory distress, Objective analysis of respiratory state (i.e., lung assessment), frequency of cough over a set period of time, radiological exam, and sera exam. In addition, the patients global assessments of response are recorded on a 6-point scale (worse, no response, fair response, good response, excellent response). Sera positive by immunofluorescence is screened for antibodies.

Cytokine Assays

Bioactive TNF are measured in sera using the WEHI 164 clone 13 cytotoxicity assay. Total 1L-6 is measured in sera using a commercial immunoassay and by a sandwich ELISA using monoclonal antibodies.

Disease Activity

The pattern of response for each of the clinical assessments of disease activity is assessed according to typical clinical assessment for SARS. Clinical assessments demonstrate improvement following the treatment. Respiratory distress decreases from a median of 2 days at entry to week 3. Similarly, the temperature and other flu like symptoms improve over the period of 24 hours to 1 week The response data is analyzed for each individual patient. Although the study is primarily designed to assess the short-term effects of treatment, follow-up clinical and laboratory data is made available for those patients followed for sufficient time. The duration of response in these patients is defined as a 20% (or greater) mean improvement in the selected activity measures or appropriate reduction of negative outcomes, such as needed for intensive care and ventilation. Comparison of the clinical and laboratory data for patients treated with oral DA dosing at each dose are compared to show differences in the rapidity or extent of response. At least about a 20% decrease in adult respiratory distress syndrome (ARDS) is observed, including each of chronic pulmonary function, diffusion capacity and lung compliance, with adequate patient tolerance. About a 40% decrease in mortality is also observed.

I claim:

1. A method for treatment of ARDS comprising administering orally a pharmaceutic composition comprising a denatonium salt, wherein the denatonium salt is selected from the group consisting of denatonium acetate (DA), denatonium citrate, denatonium maleate, and denatonium saccharide.

2. The method for treatment of ARDS of claim 1, wherein the pharmaceutical composition further comprises from about 0.5 g to about 5 g acetic acid.

3. The method for treatment of ARDS of claim 2, wherein the dosage per day of the acetic acid for an adult is from about 1.5 g to about 3 g.

4. The method for treatment of ARDS of claim 1, wherein the daily dosage of the denatonium salt for an adult is from about 10 mg to about 600 mg or from about 5 mg/kg to about 50 mg/kg body weight per day.

5. The method for treatment of ARDS of claim 1, wherein the daily dosage of the denatonium salt for an adult is from about 10 mg to about 400 mg, or to achieve a concentration in the GI tract of from about 10 parts per billion to about 10 ppm.

6. The method for treatment of ARDS of claim 1, wherein the daily total dosage of a denatonium salt for an adult is from about 20 mg to about 200 mg.

7. The method for treatment of ARDS of claim 1, wherein the daily dose of a denatonium salt is administered once per day, twice per day or three times per day.

8. A method for treatment of SARS comprising administering orally a pharmaceutic composition comprising a denatonium salt, wherein the denatonium salt is selected from the group consisting of denatonium acetate (DA), denatonium citrate, denatonium maleate, and denatonium saccharide.

9. The method for treatment of SARS of claim 8, wherein the pharmaceutical composition further comprises from about 0.5 g to about 5 g acetic acid.

10. The method for treatment of SARS of claim 9, wherein the dosage per day of the acetic acid for an adult is from about 1.5 g to about 3 g.

11. The method for treatment of SARS of claim 8, wherein the daily dosage of the denatonium salt for an adult is from about 10 mg to about 600 mg or from about 5 mg/kg to about 50 mg/kg body weight per day.

12. The method for treatment of SARS of claim 8, wherein the daily dosage of the denatonium salt for an adult is from about 10 mg to about 400 mg, or to achieve a concentration in the GI tract of from about 10 parts per billion to about 10 ppm.

13. The method for treatment of SARS of claim 8, wherein the daily total dosage of a denatonium salt for an adult is from about 20 mg to about 200 mg.

14. The method for treatment of SARS of claim 8, wherein the daily dose of a denatonium salt is administered once per day, twice per day or three times per day.

* * * * *